United States Patent [19]
Wenski et al.

[11] Patent Number: 5,072,069
[45] Date of Patent: Dec. 10, 1991

[54] CYCLOOLEFINIC COMPLEXES OF PLATINUM, PROCESSES FOR PREPARING THE SAME AND THEIR USE AS A CATALYST

[75] Inventors: Guido Wenski, München; Ludwig Maier, Eggenfelden; Hans-Jürgen Eberle, München, all of Fed. Rep. of Germany

[73] Assignee: Consortium Für Elektrochemische Ind., München, Fed. Rep. of Germany

[21] Appl. No.: 485,704

[22] Filed: Feb. 27, 1990

[30] Foreign Application Priority Data

Mar. 1, 1989 [DE] Fed. Rep. of Germany ....... 3906514

[51] Int. Cl.$^5$ ................................................ C07C 5/03
[52] U.S. Cl. ..................................... 585/277; 585/273; 585/275; 556/136; 556/137; 502/162

[58] Field of Search ..................... 556/136, 137, 9, 12; 585/700, 277, 273, 275

[56] References Cited

U.S. PATENT DOCUMENTS

| | | | |
|---|---|---|---|
| 3,439,009 | 4/1969 | Ketley | 556/136 |
| 3,932,484 | 1/1976 | Knifton | 560/114 |
| 4,065,479 | 12/1977 | Larock | 556/137 |
| 4,098,807 | 7/1978 | Stone et al. | 556/136 |
| 4,398,010 | 10/1983 | Adkins | 556/10 |

Primary Examiner—Asok Pal

[57] ABSTRACT

The invention relates to cycloolefinic complexes of platinum, process for preparing the same from platinum(II) compounds and cycloolefins having at least 12 ring carbon atoms and at least two aliphatic non-cumulated carbon-carbon double bonds and their use as a catalyst for the addition of Si-bonded hydrogen to an aliphatic multiple bond.

13 Claims, No Drawings

CYCLOOLEFINIC COMPLEXES OF PLATINUM, PROCESSES FOR PREPARING THE SAME AND THEIR USE AS A CATALYST

The invention relates to cycloolefinic complexes of platinum, processes for preparing the same from cyclic olefins and platinum (II) compounds and their use as a catalyst in the addition of Si-bonded hydrogen to an aliphatic multiple bond.

BACKGROUND OF THE INVENTION

It is known that the addition of Si-bonded hydrogen to an aliphatic multiple bond, which is frequently referred to as hydrosilylation, can be promoted by catalysts, and in particular platinum catalysts. Platinum catalysts are described, for example, in U.S. Pat. No. 3,814,730 to Karstedt, and in European Patent No. 0,032,377 to Lindner. The traditional and most widely used hydrosilylation catalyst is a solution of $H_1PtCl_6.6H_2O$ in 2-propanol, which solution contains the olefin complex $H[(C_3H_6)PtCl_3]$ as the effective component and is called the Speier catalyst after its discoverer [cf. U.S. Pat. No. 2,823,218 to Speier, Dow Corning Corporation; issued on Feb. 11, 1958, and R. A. Benkeser, J. Kang, J. Organomet. Chem. 158 (1980) C9–C12].

Platinum complexes with alicyclic dienes, such as norbornadiene-, 1,5-cyclooctadiene- and dicyclopentadiene-platinum dichloride have also been described in a Japanese Published Application 79/76 529 (Shin-Etsu Chemical Industry Co., Ltd.); Japanese Published Application 79/76 530 (Shin-Etsu Chemica Industry Co.); and U.S. Pat. No. 4,276,252 (G. Kreis, Wacker-Chemie GmbH). Even though the abovementioned platinum-catalyzed hydrosilylation processes generally give good results, they are in most cases expensive due to the large number of parts by weight of metallic platinum required to achieve the desired hydrosilylation rate.

Therefore, it is an object of the present invention to provide stable platinum complexes which are superior to the catalyst systems known heretofore in their activity and are readily meterable and can be prepared easily and in high yield. A further object of the present invention is to provide platinum complexes which are suitable for the addition reaction of monomeric or polymeric silicon compounds having Si-bonded hydrogen with monomeric or polymeric compounds having an aliphatic multiple bond.

SUMMARY OF THE INVENTION

The foregoing objects and others which will become apparent from the following description are accomplished in accordance with this invention, generally speaking, by providing cycloolefinic complexes of platinum, processes for preparing the same and their use as a catalyst, in which the cycloolefinic complexes of platinum are represented by the general formula $$(cy)_z PtX_2$$

where (cy) represents an unsubstituted or alkyl-substituted cycloolefin having at least 12 ring carbon atoms and at least two aliphatic non-cumulated carbon-carbon double bonds or a mixture of such cycloolefins, X represents the same or different halogen atoms and/or the same or different saturated or unsaturated organic radicals and/or the same or different organosilicon radicals and/or the same or different oligomeric or polymeric inorganic radicals and/or the same or different inorganic oxides and z represents a number of from 0.25 to 10, and the platinum content of the cycloolefinic complexes is from 10 to 60 percent by weight, with the proviso that 1,5,9-cyclododecatriene. $PtCl_2$ is excluded.

G. McCauley and H. Frye, in Inorg. Nucl. Chem. Letters 4 (1968) 21–4, describe the preparation of 1,5,9-cyclododecatriene-platinum dichloride. After several weeks, small amounts of yellow crystals, which can be identified as 1,5,9-cyclododecatriene-platinum dichloride, are precipitated from a benzene solution containing $Na_2PtCl_4$ and cyclododecatriene. G. McCauley and H. Frye neither disclose the catalytic property of this compound nor the possibility of preparing this complex using a molar ratio of 1,5,9-cyclododecatriene to $PtCl_2$ which differs from unity.

The unsubstituted or alkyl-substituted cycloolefins (cy) are compounds having at least 12 ring carbon atoms, preferably from 12 to 40 ring carbon atoms, and more preferably from 12 to 24 ring carbon atoms, and at least two, preferably non-cumulated and non-conjugated, carbon-carbon double bonds, in which cycloolefins having at least 14 carbon atoms are preferred.

Alkyl radicals having from 1 to 4 carbon atom(s), such as the methyl, ethyl, n-propyl, isopropyl, n-butyl, sec-butyl and tert-butyl radicals are preferred alkyl substituents of the cycloolefins, with the methyl radical being particularly preferred.

The cycloolefin present in the cycloolefinic complex of platinum may be a single type of cycloolefin. However, it may also be a mixture of at least two different types of such cycloolefins.

Examples of cycloolefins having two carbon-carbon double bonds are

| | |
|---|---|
| 1,7-cyclododecadiene | $(C_{12}H_{20})$ |
| 1,8-cyclotetradecadiene | $(C_{14}H_{24})$ |
| 1,8-cyclopentadecadiene | $(C_{15}H_{26})$ |
| 1,9-cyclohexadecadiene | $(C_{16}H_{28})$ |
| 1,13-cyclotetracosadiene | $(C_{24}H_{44})$ |
| 1,5,9,13-tetramethyl-1,9-cyclohexadecadiene | $(C_{20}H_{36})$ |

Examples of cycloolefins having three carbon-carbon double bonds are

| | |
|---|---|
| 1,7,13-cyclooctadecatriene | $(C_{18}H_{30})$ |
| 1,8,15-cycloheneicosatriene | $(C_{21}H_{36})$ |
| 1,9,17-cyclotetracosatriene | $(C_{24}H_{42})$ |
| 1,5,9-trimethyl-1,5,9-cyclododecatriene | $(C_{15}H_{24})$ |
| 1,6,11-trimethyl-1,6,11-cyclopentadecatriene | $(C_{18}H_{30})$ |

Examples of cycloolefins having four carbon-carbon double bonds are

| | |
|---|---|
| 1,5,9,13-cyclohexadecatetraene | $(C_{16}H_{24})$ |
| 1,7,13,19-cyclotetracosatetraene | $(C_{24}H_{40})$ |
| 1,9,17,24-cyclodotriacontatetraene | $(C_{32}H_{56})$ |
| 1,5,9,13-tetramethyl-1,5,9,13-cyclohexadecatetraene | $(C_{20}H_{32})$ |
| 1,6,11,16-tetramethyl-1,6,11,16-cycloeicosatetraene | $(C_{24}H_{40})$ |

Halogen atoms represented by X may be fluorine, chlorine, bromine or iodine in which chlorine is the preferred halogen atom.

The saturated or unsaturated organic radicals represented by X may be alkyl radicals, which preferably contain 1 to 4 carbon atom(s), such as methyl, ethyl, n-propyl, isopropyl, n-butyl, sec-butyl and tert-butyl radicals and more preferably the methyl and ethyl radicals; alkenyl radicals such as ethene, propene and 1-butene radicals are the preferred alkenyl radicals; enolate radicals, such as, for example, the acetylacetonate radical, and oligomeric or polymeric compounds, such as polyols and uncrosslinked butadiene rubbers or isoprene rubbers.

The radicals represented by X may furthermore be organosilicon radicals, such as, for example, an organopolysiloxane radical, oligomeric or polymeric inorganic radicals, such as, for example, phosphazenes or polyphosphates, and inorganic oxides, such as, for example, $SiO_2$, $Al_2O_3$ or zeolites.

The radicals represented by X in the cycloolefinic complex of platinum may be a single type of X radical. It may, however, also be a mixture of at least two different types of such radicals.

The number z, the molar ratio of $PtX_2$ to (cy), may have values of from 0.25 to 10; preferably z is in the range of from 0.3 to 5, and more preferably in the range of from 0.5 to 2.

The platinum content of the cycloolefinic complexes of platinum, according to this invention, is from 10 to 60 percent by weight, and more preferably from 30 to 50 percent by weight.

The relationship between the platinum content $p_{pt}$ of the cycloolefinic complexes of platinum, according to this invention, and the molar ratio z may be expressed by the following formula:

$$z = \frac{(M_{(cy)}/M_{Pt}) \cdot p_{Pt}}{100 - (M_{PtX_2}/M_{Pt}) \cdot p_{Pt}}$$

$M_{(cy)}$: Molecular weight of the cycloolefin
$M_{Pt}$: Atomic weight of platinum
$M_{PtX_2}$: Molecular weight of $PtX_2$
$p_{pt}$: Platinum content of the cycloolefin complex in percent by weight.

Examples of cycloolefinic complexes of platinum, according to this invention, are

| | |
|---|---|
| $(C_{12}H_{18}) \cdot zPtBr_2$ | z = 0.3–3 |
| $(C_{14}H_{24}) \cdot zPtCl_2$ | z = 0.3–2 |
| $(C_{15}H_{24}) \cdot zPt(CH_3)_2$ | z = 0.3–3 |
| $(C_{16}H_{24}) \cdot zPt(CH_3)Cl$ | z = 0.5–4 |
| $(C_{21}H_{36}) \cdot zPt(C_2H_5)_2$ | z = 0.5–3 |
| $(C_{24}H_{44}) \cdot zPtI_2$ | z = 0.5–2 |
| $(C_{24}H_{40}) \cdot zPtCl_2$ | z = 0.6–4 |
| $(C_{32}H_{56}) \cdot zPt(CH_3)Br$ | z = 0.6–4. |

Preferred cycloolefinic complexes of platinum are
$(C_{12}H_{18}) \cdot 0.62 \, PtCl_2$
$(C_{15}H_{24}) \cdot 1.57 \, PtCl_2$
$(C_{15}H_{24}) \cdot 1.02 \, PtCl_2$
$(C_{16}H_{24}) \cdot 1.20 \, PtCl_2$
$(C_{24}H_{42}) \cdot 2.46 \, PtCl_2$
$(C_{24}H_{42}) \cdot 1.60 \, PtCl_2$
$(C_{32}H_{56}) \cdot 1.49 \, PtCl_2$.

The cycloolefinic complexes of platinum, according to this invention, having the general formula $(cy) \cdot zPtX_2$, in which (cy), z and X are the same as above, can be prepared by reacting an unsubstituted or alkyl-substituted cycloolefin having at least 12 ring carbon atoms and at least two aliphatic non-cumulated carbon-carbon double bonds or a mixture of such cycloolefins with a platinum compound of the general formula $M_aPtY_b \cdot nH_2O$, in which M may be the same or different and represents hydrogen, an alkali metal or ammonium which may be substituted by alkyl groups, preferably alkyl groups having from 1 to 4 carbon atom(s); Y has the same meaning as X; a is 0, 1 or 2, b is 2, 3 or 4; n is an integer between 0 and 6 and b is equal to a + 2, with the proviso that the platinum(II) compound may be in the form of a complex with aliphatic unsaturated hydrocarbons, preferably aliphatic unsaturated hydrocarbons having from 2 to 6 carbon atoms, or a mixture of such platinum compounds, at temperatures of from 0° to 60° C., and more preferably between 20° and 25° C., with stirring in the presence of an organic solvent. The reaction is generally complete after 2 to 4 days.

Preferred radicals represented by Y are halogen atoms, such as fluorine, chlorine, bromine or iodine and saturated or unsaturated organic radicals.

The saturated or unsaturated organic radicals represented by Y may be alkyl radicals, which preferably contain 1 to 4 carbon atom(s), such as the methyl, ethyl, n-propyl, isopropyl, n-butyl, sec-butyl and tert-butyl radicals; alkenyl radicals, preferably ethene, propene and 1-butene radicals and enolate radicals, such as, for example, the acetylacetonate radical.

The platinum compounds to be used according to this invention are preferably platinum dihalides, such as $PtCl_2 \cdot nH_2O$ and $PtBr_2 \cdot nH_2O$ and $PtI_2 \cdot nH_2O$, tetrahalogenoplantinic acids, such as $H_2PtCl_4 \cdot nH_2O$ and $H_2PtBr_4 \cdot nH_2O$, salts of tetrahalogenoplatinic acids, such as $Na_2PtCl_4 \cdot nH_2O$, $K_2PtCl_4$, $KHPtCl_4 \cdot nH_2O$, $(NH_4)_2PtCl_4$, $Na_2PtBr_4$ and $K_2PtBr_4$, and platinum halide complexes with aliphatic unsaturated hydrocarbons, such as $K[(C_2H_4)PtCl_3]$, $[(C_2H_4) \cdot PtCl_2]_2$ and $[(C_3H_6) \cdot PtCl_2]_2$, wherein n is the same as above, with the proviso that hydrated platinum halide complexes are particularly preferred.

The platinum compound used in the process of this invention may be a single type of platinum compound or may be a mixture of at least two different types of such platinum compounds.

In the process of this invention, preferably polar organic solvents are used, if necessary in admixture with water.

Examples of such solvents are alcohols, such as methanol, ethanol, n-propanol, isopropanol and n-butanol, carboxylic acids, such as, for example, acetic acid, chlorinated hydrocarbons, such as dichloromethane, trichloromethane, tetrachloromethane, 1,2-dichloroethane and trichloroethylene, and ketones, such as acetone, methyl ethyl ketone and methyl isobutyl ketone.

In the process of this invention, polar protic solvents, such as methanol, ethanol, n-propanol, isopropanol, n-butanol and acetic acid, mixtures of at least two types of such solvents and mixtures of at least one type of such solvent with water are particularly preferred in which not more than 60 percent by weight of water is present in the mixture.

In the process of this invention, the cycloolefins (cy) described above can preferably be used in the form of a cis/trans-isomeric mixture, the preparation of which is known per se. For example, the cyclodiolefins used according to this invention can be prepared by a metathetic method according to U.S. Pat. No. 4,668,836 (H.J. Eberle) or the corresponding German Offenlegungsschrift 3,524,977 (issued on May 22, 1986). In this procedure, the cyclodiolefins are prepared in the liquid phase by metathesis of cycloalkylenes in the presence of a supported catalyst based on $Re_2O_7/Al_2O_3$. The preparation of cyclopolyolefins can be carried out, for example, according to K. J. Ivin, "Olefin Metathesis", Academic Press, London, 1983.

In the process of this invention, the molar ratio of cycloolefin (cy) to platinum compound in the reaction solution can have values of from 0.1 to 10, preferably from 0.8 to 5, and more preferably from 1 to 3.

In the process of this invention, the platinum concentration of the reaction solution is from 0.05 to 0.25 mol/l and more preferably the platinum concentration is from 0.10 to 0.12 mol/l.

The process of this invention is preferably carried out under a pressure of from 900 to 1100 hPa (absolute), or if desired, at higher or lower pressures.

In the process of this invention, the radicals represented by X of the cycloolefinic complexes of platinum having the general formula $(cy).zPtX_2$, wherein (cy), z and X are the same as above, can be determined directly by the choice of the corresponding educts. Another possibility is to subject the cycloolefinic complex of this invention to an exchange reaction, in which the desired radical X is introduced into the cycloolefinic complex of platinum preferably via the corresponding compound MX, with the proviso that M and X have the meaning above and X in MX differs from the radical X to be exchanged in the platinum complex. In the process for preparing halogen-free cycloolefinic complexes of platinum according to this invention, the exchange reaction is preferred.

After the reaction of an unsubstituted or alkyl-substituted cycloolefin having at least 12 carbon atoms and at least two aliphatic non-cumulated carbon-carbon double bonds, or a mixture of such cycloolefins, with a platinum compound of the formula $M_aPt^{II}Y_b \cdot nH_2O$, wherein M, Y, a, b and n are the same as above, with the proviso that the platinum (II) compound may be in the form of a complex with aliphatic unsaturated hydrocarbons, or a mixture of such platinum compounds, is complete, the reaction mixture is worked up by methods known per se, such as, for example, crystallization, reprecipitation and filtration. The cycloolefinic complex of platinum, according to this invention, is obtained in a yield of preferably from 50 to 90 percent, based on elemental platinum.

Insufficient working up of the reaction mixture may lead to deviations in the average empirical formula of the cycloolefinic complexes of platinum, for example, in accordance with $(cy).zPtX_c$, wherein c may assume values differing from two and (cy), z and X are the same as above.

The cycloolefins of platinum of this invention can be used as a catalyst wherever monomeric or polymeric silicon compounds having Si-bonded hydrogen are to be subjected to an addition reaction with monomeric or polymeric compounds having an aliphatic multiple bond. In this addition reaction, other monomeric, dimeric or polymeric, silicon-containing compounds may be formed or modified, depending on the choice of the compounds to be subjected to the addition reaction.

In the process of this invention a silicone compound having Si-bonded hydrogen is added to an aliphatic multiple bond in the addition reaction, in which the amounts of cycloolefinic complex of platinum used can be the same as used heretofore in the addition reaction for adding a Si-bonded hydrogen to an aliphatic multiple bond. Because of the high efficiency and the high initial activity of the cycloolefinic complexes of platinum as a catalyst, concentrations of preferably from 0.1 to 100 ppm by weight, and more preferably from 1 to 50 ppm by weight of platinum, calculated as elemental platinum in the reaction mass, are sufficient for achieving a high conversion and short reaction times in the addition of Si-bonded hydrogen to an aliphatic multiple bond.

In the process of this invention, for the addition of Si-bonded hydrogen to an aliphatic multiple bond, the temperatures and pressures used may, likewise, be the same as used heretofore in the known processes for the addition of Si-bonded hydrogen to an aliphatic multiple bond. Since the cycloolefinic complexes of platinum of this invention have a high efficiency and a high initial activity, the addition of Si-bonded hydrogen to an aliphatic multiple bond can be carried out at low temperatures, preferably at temperatures of from $-20°$ to $200°$ C., and more preferably from $15°$ to $110°$ C., and under a pressure of preferably from 900 to 1100 hPa (absolute), without having to accept a low conversion and long reaction times.

Examples of monomeric silicon compounds which can be prepared using the cycloolefinic complexes of platinum of this invention as a catalyst, are the preparation of 3-chloropropyltrichlorosilane by reacting trichlorosilane with allyl chloride; the preparation of 3-chloropropylmethyldi-chlorosilane by reacting methyldichlorosilane with allyl chloride; the preparation of n-propyltrichlorosilane by reacting propene with trichlorosilane; the preparation of methacryloxypropyltrichlorosilane by reacting allyl methacrylate with trichlorosilane and the preparation of vinyl-methyldichlorosilane by reacting acetylene with methyldichlorosilane.

Examples of dimeric or polymeric, silicon-containing compounds, which can be prepared using the cycloolefinic complexes of platinum according to this invention as a catalyst, are the reaction of vinyltrichlorosilane with trichlorosilane to form bis-(1,2-trichlorosilyl)-ethane and the preparation of organosiloxanes with SiC-bonded ester groups by an addition reaction of at least one diester of allylsuccinic acid with an organosiloxane having Si-bonded hydrogen.

The modification of polymeric, silicon-containing compounds, in which the cycloolefinic complexes of platinum of this invention can be used as a catalyst, includes, in particular, the crosslinking, i.e., curing or vulcanization of materials based on organopolysiloxanes containing alkenyl groups, especially vinyl groups, and Si-bonded hydrogen. The essential components of such materials, other than the cycloolefinic complexes of platinum (a) of this invention, are (b) diorganopolysiloxanes containing alkenyl groups and in particular diorganopolysiloxanes of the formula

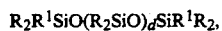

wherein R represents the same or different, monovalent, SiC-bonded organic radicals which are free of aliphatic carbon-carbon multiple bonds, R1 represents the same or different SiC-bonded organic radicals having an aliphatic carbon-carbon multiple bond and d represents an integer having a value such that the mean viscosity of these diorganopolysiloxanes is 100 to $10^6$ mPa.s at $25°$ C., (c) compounds having Si-bonded hydrogen, preferably linear, cyclic or branched organopolysiloxanes consisting of units of the formula

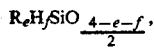

wherein R is the same as above, e is 0, 1, 2 or 3, f is 0 or 1 and the sum of e +f is 0, 1, 2 or 3, with the proviso that there are at least two Si-bonded hydrogen atoms per molecule.

The preparation of the crosslinkable materials based on organopolysiloxanes containing alkenyl groups and Si-bonded hydrogen can be carried out by mixing the constituents by methods conventionally used for the preparation of materials which are crosslinkable by addition of Si-bonded hydrogen to an aliphatic multiple bond, in which one component contains constituent (a) and constituent (b) and a second component which contains constituent(c), particularly in the case of materials which are crosslinkable at temperatures as low as room temperature.

The cycloolefinic complexes of platinum of this invention are used as a catalyst in the crosslinking of materials based on organopolysiloxanes containing alkenyl groups and Si-bonded hydrogen which may be, for example, used as embedding materials for electrical or electronic apparatuses or coating materials, including materials for the production of coatings which repel tacky substances, for example, on paper, or molding materials, for example, for the production of concrete moldings, and in particular for the production of impressions of human or animal teeth.

When the cycloolefinic complexes of platinum are used as a catalyst, it is of course also possible, if necessary to concomitantly use agents which retard the addition of Si-bonded hydrogen to an aliphatic multiple bond, such as benzotriazole, 1,3-divinyl-1,1,3,3-tetramethyldisiloxane and/or 2-methylbut-3-yn-2-ol at room temperature.

Furthermore, the cycloolefinic complexes of platinum may be used as a catalyst for reactions closely related to hydrosilylation, such as isomerization of alkenes, described, for example, in A. J. Hubert and U. Reinhinger, Synthesis (1970) 405–30, hydrogenation of alkenes, described, for example, in B. R. James, Advances in Organometallic Chemistry 17 (1979) 319–405, and hydroformylation of alkenes, described, for example, in R. L. Pruett, Advances in Organometallic Chemistry 17 (1979) 1–60.

The cycloolefinic complexes of platinum, when used as a catalyst in the addition of Si-bonded hydrogen to an aliphatic multiple bond have the advantage that, on the one hand, because of their high efficiency or their high initial activity, it is possible to use lower concentrations of catalyst in the reaction mixture than those required in the case of the hydrosilylation catalysts known heretofore and, on the other hand, shorter reaction times and lower temperatures are sufficient for a high conversion. In addition, the cycloolefinic complexes of platinum of this invention are very stable.

Another advantage is the good meterability of the cycloolefinic complexes of platinum of this invention. Owing to their very good solubility in conventional polar organic solvents, such as dichloromethane, trichloromethane or acetone and, in particular, cycloolefinic complexes of platinum having three or four aliphatic non-cumulated carbon-carbon double bonds can be incorporated into the reaction masses in general homogeneously and hence completely without turbidity, especially into the reaction masses based on organopolysiloxanes containing alkenyl groups and Si-bonded hydrogen.

In the following examples, all parts are by weight unless otherwise specified.

Unless specified otherwise, the cycloolefins used were prepared by the processes described above. All cycloolefins used are in the form of a cis/trans-isomer mixture.

All infrared data were obtained with KBr disks.

EXAMPLE 1

About 2.00 g of $Na_2PtCl_4.4H_2O$ are dissolved in 40 ml of n-propanol, then 0.80 g of 1,5,9-cyclododecatriene ($C_{12}H_{18}$; commercially available from Aldrich-Chemie GmbH & Co. KG, D-7924 Steinheim) is added and the mixture is stirred at room temperature. After 3 days, a clear yellow solution with a grey pulverulent precipitate is obtained. The precipitate is isolated and identified as NaCl. The filtrate is freed from solvent in vacuo and the remaining yellow solid is washed twice with 60 ml of n-hexane. After the solid has been dried in vacuo, 1.98 g of a yellow powder are obtained, which according to elemental analysis contains 37.1 percent by weight of platinum. The yield is 86 percent based on elemental platinum.

In the infrared spectrum, the cyclododecatriene complex of platinum has significant bands at 339, 706, 860, 966, 983, 1041, 1188, 1439, 1459, 1544, 2842, 2866, 2907, 2933 and 3006 $cm^{-1}$.

EXAMPLE 2

About 2.00 g of $Na_2PtCl_4.4H_2O$ are dissolved in 40 ml of n-propanol, then 0.88 g of trimethyl-1,5,9-cyclododecatriene ($C_{15}H_{24}$; mixture of 1,5,9-trimethyl- and 3,7,11-trimethyl compounds; commercially available from Deutsche Shell Chemie GmbH, D-6236 Eschborn) is added and the mixture is stirred at room temperature. After 4 days, the precipitated NaCl is filtered off and the filtrate is freed from solvent in vacuo. A brown residue of oily consistency is dissolved in 10 ml of dichloromethane. After further filtration, the filtrate is freed from solvent in vacuo, and 20 ml of n-hexane are then added while stirring. The solid is separated off and then washed three times with 15 ml of n-hexane and dried in vacuo. About 1.47 g of a pale brown powder is obtained, which according to elemental analysis contains 49.2 percent by weight of platinum. The yield is 84 percent, based on elemental platinum.

In the infrared spectrum, the trimethylcyclododecatriene complex of platinum has significant bands at 1028, 1380, 1434, 1451, 1623 and about 2930 (broad) $cm^{-1}$.

EXAMPLE 3

The procedure described in Example 2 is repeated, except that 1.20 g of trimethyl-1,5,9-cyclododecatriene are substituted for the 0.88 g of trimethyl-1,5,9-cyclododecatriene. About 1.66 g of a pale brown powder, which according to elemental analysis contains 41.8 percent by weight of platinum are obtained. The yield is 81 percent, based on elemental platinum.

In the infrared spectrum, the trimethylcyclododecatriene complex of platinum has significant bands at 1028, 1380, 1434, 1451, 1623 and about 2930 (broad) $cm^{-1}$.

EXAMPLE 4

The procedure described in Example 2 is repeated, except that 1.10 g of 1,5,9,13-cyclohexadecatetraene ($C_{16}H_{24}$) are substituted for the 0.88 g of trimethyl-1,5,9-cyclododecatriene and n-pentane is substituted for the n-hexane. About 0.92 g of a pale brown powder is obtained, which according to elemental analysis contains 43.7 percent by weight of platinum. The yield is 47 percent, based on elemental platinum.

In the infrared spectrum, the cyclohexadecatetraene complex of platinum has significant bands at 332, 1436, 1452, 1620, 1708, 2870 and about 2930 (broad) $cm^{-1}$.

EXAMPLE 5

About 2.00 g of $Na_2PtCl_4.4H_2O$ are dissolved in 20 ml of n-propanol, then 1.60 g of 1,9,17-cyclotetracosatriene ($C_{24}H_{42}$) are added and the mixture is stirred at room temperature. After three days, the precipitated NaCl is filtered off and the filtrate is freed from solvent in vacuo. The brown residue of oily consistency is worked up in accordance with the procedure described in Example 2. About 1.20 g of a yellow powder, which according to elemental analysis contains 48.7 percent by weight of platinum, are obtained. The yield is 68 percent, based on elemental platinum.

In the infrared spectrum, the cyclotetracosatriene complex of platinum has significant bands at 359, 723, 1350, 1456, 1506, 2855 and 2927 $cm^{-1}$.

EXAMPLE 6

The procedure described in Example 5 is repeated, except that 2.90 g of 1,9,17-cyclotetracosatriene are substituted for the 1.60 g of 1,9,17-cyclotetracosatriene. About 1.86 g of a yellow powder, which according to elemental analysis contains 41.3 percent by weight of platinum, are obtained. The yield is 90 percent, based on elemental platinum.

In the infrared spectrum, the cyclotetracosatriene complex of platinum has significant bands at 339, 725, 1360, 1460, 1510, 1619, 2855 and 2926 $cm^{-1}$.

EXAMPLE 7

About 2.00 g of $Na_2PtCl_4.4H_2O$ are dissolved in 40 ml of n-propanol, then 10.00 g of 1,9,17,25-cyclodotriacontatetraene ($C_{32}H_{56}$) are added and the mixture is stirred at room temperature. After 3.5 days, the precipitated NaCl is filtered off and the filtrate is freed from solvent in vacuo. The brown residue of oily consistency is worked up in accordance with the procedure described in Example 1. About 1.31 g of a brown powder, which according to elemental analysis contains 34.7 percent by weight of platinum, are obtained. The yield is 53 percent, based on elemental platinum.

In the infrared spectrum, the cyclodotriacontatetraene complex of platinum has significant bands at 330, 724, 969, 1461, 1622, 2856 and 2926 $cm^{-1}$.

EXAMPLE 8

About 2.00 g of $Na_2PtCl_4.4H_2O$ are dissolved in 40 ml of n-propanol, then 2.12 g of 1,8-cyclotetradecadiene ($C_{14}H_{24}$) are added and the mixture is stirred for 2.5 days at room temperature. The platinum complex thus formed is precipitated along with the NaCl. After the solvent has been removed by distillation, the yellow residue is suspended in 120 ml of distilled water, the suspension is filtered and the residue is washed twice each with 30 ml of distilled water. The solid is then stirred twice each with 30 ml of methanol and three times each with 30 ml of dichloromethane, filtered each time and then dried in vacuo. About 2.00 g of a yellow powder are obtained, which according to elemental analysis contains 36.8 percent by weight of platinum. The yield is 86 percent, based on elemental platinum.

In the infrared spectrum, the cyclotetradecadiene complex of platinum has significant bands at 338, 791, 857, 974, 1258, 1445, 1538, 2856 and 2929 $cm^{-1}$.

EXAMPLE 9

About 2.00 g of $Na_2PtCl_4.H_2O$ are dissolved in 40 ml of n-propanol, then 1.50 g of 1,13-cyclotetracosadiene ($C_{24}H_{44}$) are added and the mixture is stirred for 4 days at room temperature. The platinum complex thus formed is precipitated along with the NaCl. The precipitate is filtered off and washed twice each with 15 ml of n-propanol. A greyish yellow powder is obtained which is suspended in 20 ml of dichloromethane. The suspension is filtered and the residue is washed with dichloromethane and then dried.

The powder is then suspended in a mixture of 25 ml of water and 3 ml of acetone and stirred for 2 hours. The suspension is filtered and the residue is washed with water and acetone and dried in vacuo. About 1.03 g of a pale yellow powder are obtained, which according to elemental analysis contains 32.5 percent by weight of platinum. The yield is 39 percent, based on elemental platinum. In the infrared spectrum, the cyclotetracosadiene complex of platinum has significant bands at 338, 720, 841, 913, 1033, 1349, 1452, 1468, 1541, 2850, and 2922 $cm^{-1}$.

EXAMPLE 10

A certain amount of the cycloolefinic complex of platinum from Examples 1 to 6 is dissolved in each case in a little dichloromethane, and the cycloolefinic complex of platinum from Example 7 is dissolved in a little acetone, and the solutions thus obtained are each mixed with 100 g of a dimethylpolysiloxane containing vinyldimethylsiloxy terminal units and having a viscosity of 1300 mPa.s at a temperature of 25° C. The particular mixture is stirred at room temperature and under a pressure of 1 hPa (absolute) until the solvent has evaporated. The amount of each platinum complex to be used (about 4 to 6 mg) depends on its platinum content and is calculated so that the platinum content, based on elemental platinum, of the dimethylpolysiloxane containing vinyldimethylsiloxy terminal units is 20 ppm.

The dimethylpolysiloxane containing the particular cycloolefinic complex of platinum and having vinyldimethylsiloxy terminal units is stored for 2 hours at a temperature of 25° C. Thereafter, 0.5 g of a copolymer of dimethylsiloxane, methylhydrogensiloxane and trimethylsiloxane units is stirred into 4.5 g of this mixture, the molar ratio of the dimethylsiloxane units to the methylhydrogensiloxane units being 9:1 and the copolymer having a viscosity of 500 mPa.s at a temperature of 25° C.

The time between the beginning of mixing and marked crosslinking of the material (crosslinking time) is shown in Table 1 for the particular cycloolefinic complex of platinum. This time is indirectly proportional to the catalytic activity of the particular cycloolefinic complex of platinum.

TABLE 1

| Cycloolefinic complex of platinum from Example | (cy) | Molar ratio of the educts (cy):Pt | Yield, based on platinum in % | Platinum content in % by weight | z | Crosslinking time in seconds |
|---|---|---|---|---|---|---|
| 1 | $C_{12}H_{18}$ | 1.25 | 86 | 37.1 | 0.62 | 43 |
| 2 | $C_{15}H_{24}$ | 1.00 | 84 | 49.2 | 1.57 | 94 |
| 3 | $C_{15}H_{24}$ | 1.20 | 81 | 41.8 | 1.02 | 40 |
| 4 | $C_{16}H_{24}$ | 1.12 | 47 | 43.7 | 1.20 | 47 |
| 5 | $C_{24}H_{42}$ | 1.10 | 68 | 48.7 | 2.46 | 120 |
| 6 | $C_{24}H_{42}$ | 2.00 | 90 | 41.3 | 1.60 | 85 |
| 7 | $C_{32}H_{56}$ | 5.00 | 53 | 34.7 | 1.49 | 43 |

EXAMPLE 11

The procedure of Example 10 is repeated, except that a certain amount of cycloolefinic complex of platinum from Examples 8 and 9 is suspended in each case in a little dichloromethane and mixed in each case with 100 g of a dimethylpolysiloxane containing vinyldimethylsiloxy terminal units.

TABLE 2

| Cycloolefinic complex of platinum from Example | (cy) | Molar ratio of the educts (cy):Pt | Yield, based on platinum in % | Platinum content in % by weight | z | Crosslinking time in seconds |
|---|---|---|---|---|---|---|
| 8 | $C_{14}H_{24}$ | 2.50 | 86 | 36.8 | 0.73 | 230 |
| 9 | $C_{24}H_{44}$ | 1.10 | 39 | 32.5 | 0.99 | 107 |

COMPARISON EXAMPLE 1

Dicyclopentadieneplatinum dichloride (dicpPtCl$_2$) according to U.S. Pat. No. 4,276,252 (G. Greis, Wacker-Chemie GmbH) is prepared by a method known from the literature (J. Chatt, L. M. Vallarino and L. M. Venanzi, J. Chem. Soc. (London) (1957) 2496-505 and H. C. Clark and L. E. Manzer, J. Organometal. Chem. 59 (1973) 411-28. About 7.00 g of K$_2$PtCl$_4$ are dissolved in 120 ml of water, and 90 ml of n-propanol, 11.5 g of dicyclopentadiene and 60 mg of anhydrous SnCl$_2$ are added. A voluminous precipitate is formed after stirring for 2 days at room temperature. The precipitate is filtered off and washed with water, a little ethanol and then n-hexane. The precipitate is dissolved in dichloromethane and then precipitated at a temperature of −80° C. with the addition of n-hexane. After filtration and drying, 5.70 g of dicpPtCl$_2$ is recovered as a pale powder, which according to elemental analysis contains 49.0 percent by weight of platinum. The yield is 85 percent, based on elemental platinum.

In the infrared spectrum, dicpPtCl$_2$ shows significant bands at 310, 331, 630, 725, 813, 832, 851, 898, 920, 948, 996, 1170, 1218, 1241, 1269, 1299, 1333, 1423, 1452, 2881, 2980 and 3038 cm$^{-1}$.

A certain amount of dicpPtCl$_2$ is dissolved in dichloromethane. The procedure described in Example 10 is repeated in which a slight turbidity of the dicpPtCl$_2$-siloxane mixture is observed.

The crosslinking time is 380 seconds.

COMPARISON EXAMPLE 2

Norbornadieneplatinum dichloride (norPtCl$_2$) according to Japanese Application 79/76 529 (Shin-Etsu Chemical Industry Co., Ltd.) and Japanese Application 79/76 530 (Shin-Etsu Chemical Industry Co. Ltd.;) is prepared by methods known from the literature (E.W. Abel, M. A. Bennett and G. Wilkinson, J. Chem. Soc. (London) (1959), 3178-82, H. C. Clark and L. E. Manzer, J. Organometal. Chem. 59 (1973) 411-28, and R. A. Alexander, N. C. Baenziger, C. Carpenter and J. R. Doyle, J. Am. Chem. Soc. 82 (1960) 535-8.

About 5.00 g of K$_2$PtCl$_4$ are dissolved in a mixture containing 100 ml of water and 75 ml of n-propanol, then 50 mg of anhydrous SnCl$_2$ and 3 ml of norbornadiene are added and the mixture is stirred for 4 days at room temperature. A white precipitate is formed, which is filtered off and washed with n-hexane. After the precipitate has been dried in vacuo, 1.70 g of norPtCl$_2$ are obtained as a white powder, which according to elemental analysis contains 54.5 percent by weight of platinum. The yield is 40 percent, based on elemental platinum.

In the infrared spectrum, norPtCl$_2$ has significant bands at 292, 324, 342, 777, 801, 850, 972, 1183, 1229, 1312, 1391, 1438, 2930, 2961, 3057 and 3070 cm$^{-1}$.

A certain amount of norPtCl$_2$ is suspended in dichloromethane. The procedure described in Example 10 is repeated in which substantial turbidity of the norPtCl$_2$-siloxane mixture is observed.

The crosslinking time is 450 seconds.

EXAMPLE 12

About 8.61 g of allyl acetate and 10 g of triethylsilane silane [HSi(C$_2$H$_5$)$_3$] are introduced into a flask equipped with a reflux condenser and stirred at a temperature of 40° C. The cycloolefinic complexes of platinum of Examples 1, 3 and 8 are each added in solid form in an amount such that the platinum content of the reaction mixture is 50 ppm, based in each case on elemental platinum.

In order to monitor the course of the reaction, samples are taken at certain times and the content of the 3-adduct (3-triethylsilylpropyl ester of acetic acid) is determined mined by gas chromatography. Table 3 shows the content of the 3-adduct in the reaction mixture, in percent by weight, during the addition reaction of triethylsilane with allyl acetate as a function of the reaction time.

TABLE 3

| Cycloolefinic complex of platinum from Example | Reaction time in minutes at 40° C. | | |
|---|---|---|---|
| | 15 | 50 | 150 |
| 1 | 18.3 | 56.0 | 84.8 |
| 3 | 25.3 | 61.4 | 84.3 |
| 8 | 16.9 | 43.1 | 84.0 |

COMPARISON EXAMPLE 3

The procedure described in Example 12 is repeated, except that instead of the cycloolefinic complexes of platinum from Examples 1, 3 and 8, dicyclopentadieneplatinum dichloride described in U.S. Patent No. 4,276,252 (G. Kreis, Wacker-Chemie GmbH) from Comparative Example 1 is used.

Table 4 shows the content of the 3-adduct in the reaction mixture, in percent by weight, during the addition reaction of triethylsilane with allyl acetate as a function of the reaction time.

TABLE 4

| Cycloolefinic complex of platinum | Reaction time in minutes at 40° C. | | |
|---|---|---|---|
| | 15 | 50 | 150 |
| dicpPtCl$_2$ | 8.9 | 36.6 | 83.3 |

What is claimed is:

1. A cycloolefinic complex of platinum having the general formula (cy).zPtX$_2$, in which (cy) is selected from the group consisting of an unsubstituted cycloolefin having at least 12 ring carbon atoms and at least two aliphatic non-cumulated carbon-carbon double bonds, and alkyl substituted cycloolefin having at least 12 ring carbon atoms and at least two aliphatic non-cumulated carbon-carbon double bonds and mixtures of such cycloolefins, X is selected from the group consisting of halogen atoms, alkyl radicals having 1 to 4 carbon atom(s), alkenyl radicals, enolate radicals, polyols, uncrosslinked rubber selected from the group consisting of butadiene and isoprene, organosilicon radicals, oligomeric and polymeric inorganic radicals selected from the group consisting of phosphazenes and polyphosphates, inorganic oxides selected from the group consisting of SiO$_2$O$_3$ and zeolites and mixtures thereof and z is a number of from 0.25 to 10, in which the platinum content of the cycloolefinic complex is from 10 to 60 percent by weight, with the proviso that 1,5,9-cyclododecatriene PtCl$_2$ is excluded.

2. The cycloolefinic complex of claim 1, wherein (cy) is an unsubstituted cycloolefin having 12 to 40 ring carbon atoms.

3. The cycloolefinic complex of claim 1, wherein (cy) is an alkyl-substituted cycloolefin having 12 to 40 ring carbon atoms.

4. The cycloolefinic complex of platinum of claim 1, wherein (cy) is an unsubstituted cycloolefin having three or four aliphatic non-cumulated double bonds.

5. The cycloolefinic complex of claim 1, wherein (cy) is an alkyl-substituted cycloolefin having three or four aliphatic non-cumulated double bonds.

6. The cycloolefinic complex of platinum of claim 1, wherein z is a number between 0.3 and 5.

7. A process for preparing the cycloolefinic complexes of platinum of claim 1, wherein a cycloolefin selected from the group consisting of an unsubstituted cycloolefin having at least 12 ring carbon atoms and at least two aliphatic non-cumulated carbon-carbon double bonds, an alkyl-substituted cycloolefin having at least 12 ring carbon atoms and at least two aliphatic non-cumulated carbon-carbon double bonds and mixtures of such cycloolefins, is reacted with a platinum compound of the formula M$_a$PtY$_b$.nH$_2$O, in which M is selected from the group consisting of hydrogen, alkali metal and ammonium which may be substituted by alkyl groups, Y has the same meaning as X, a is 0, 1 or 2, b is 2, 3 or 4, n is an integer between 0 and 6 and b is equal to a + 2, with the proviso that the platinum (II) compound may be in the form of a complex with aliphatic unsaturated hydrocarbons or a mixture of such platinum compounds, in a molar ratio of 0.1 to 10, in the presence of an organic solvent, and, if required, the radicals X present in the resulting cycloolefin complex of platinum, X is selected from the group consisting of halogen atoms, saturated organic radicals, unsaturated organic radicals, organosilicon radicals, oligomeric inorganic radicals, polymeric inorganic radicals, inorganic oxides and mixtures thereof, are then replaced by an exchange reaction by MX, M and X having the above mentioned meaning and X in MX differs from the radical X to be exchanged in the platinum complex.

8. The process of claim 7, wherein the platinum concentration of the reaction mixture is 0.05 to 0.25 mol/l.

9. The process of claim 7, wherein the organic solvent is polar.

10. The process of claim 8, wherein the organic solvent is polar.

11. The process of claim 7, wherein the molar ratio of the unsubstituted or alkyl-substituted cycloolefin having at least 12 ring carbon atoms and at least two aliphatic non-cumulated carbon-carbon double bonds, or the mixture of such cycloolefins, to the platinum compound of the general formula M$_a$PtY$_b$.nH$_2$O, in which M is selected from the group consisting of hydrogen, alkali metal and ammonium which may be substituted by alkyl groups, Y is selected from the group consisting of halogen atoms, saturated organic radicals, unsaturated organic radicals, organosilicon radicals, oligomeric inorganic radicals, polymeric inorganic radicals, inorganic oxides and mixtures thereof, a is 0, 1 or 2, b is 2, 3 or 4, n is an integer between 0 and 6 and b is equal to a + 2, with the proviso that the platinum (II) compound may be in the form of a complex with aliphatic unsaturated hydrocarbons, or the mixture of such platinum compounds, is 0.8–5.

12. An organosilicon composition containing the cycloolefinic complex of claim 1.

13. A process for preparing saturated hydrocarbons which comprises contacting alkenes with a hydrogen source in the presence of the cycloolefinic complexes of platinum of claim 1.

* * * * *

UNITED STATES PATENT AND TRADEMARK OFFICE
CERTIFICATE OF CORRECTION

PATENT NO. : 5,072,069

DATED : December 10, 1991

INVENTOR(S) : Guido Wenski, Ludwig Maier, and Hans-Jürgen Eberle

It is certified that error appears in the above-identified patent and that said Letters Patent is hereby corrected as shown below:

Column 13, line 27, after consisting, delete "$SiO_2O_3$" and insert

--- $SiO_2$, $Al_2O_3$ ---.

Signed and Sealed this

Twentieth Day of April, 1993

*Attest:*

MICHAEL K. KIRK

*Attesting Officer*     *Acting Commissioner of Patents and Trademarks*